United States Patent [19]

Ippommatsu et al.

[11] Patent Number: 4,897,628
[45] Date of Patent: Jan. 30, 1990

[54] GAS SENSOR AND METHOD OF MANUFACTURING THE SAME

[75] Inventors: Masamichi Ippommatsu, Hyogo; Takeshi Matsumoto, Osaka; Shingo Yakushizi, Osaka; Katsuyuki Kuroki, Osaka; Takashi Matsuzaka, Shizuoka, all of Japan

[73] Assignees: Osaka Gas Co., Ltd., Osaka; Kabushiki Kaisha Toshiba, Kawasaki, both of Japan

[21] Appl. No.: 116,986

[22] Filed: Nov. 5, 1987

[30] Foreign Application Priority Data

Nov. 5, 1986 [JP]  Japan .......................... 61-170831[U]
Mar. 18, 1987 [JP] Japan .................. 62-64834

[51] Int. Cl.$^4$ ............................................ H01L 7/00
[52] U.S. Cl. ...................................... 338/34; 338/306; 338/308

[58] Field of Search .......................... 338/34, 306–308; 73/23; 29/610 R

[56] References Cited

U.S. PATENT DOCUMENTS 4,574,264  3/1986  Takahashi et al. ..................... 338/34
4,592,967  6/1986  Komatsu et al. ................. 338/34 X
4,697,165  9/1987  Ishiguro et al. ........................ 338/34
4,732,738  3/1988  Nakatani et al. ................. 338/34 X Primary Examiner—Bruce A. Reynolds
Assistant Examiner—M. M. Lateef
Attorney, Agent, or Firm—Cushman, Darby & Cushman

[57] ABSTRACT

A gas sensor using an n-type metal oxide semiconductor and a method for manufacturing such a gas sensor is provided. More particularly, a gas sensor for detecting an inflammable gas and a method for manufacturing the same.

7 Claims, 5 Drawing Sheets

GAS SENSOR AND METHOD OF MANUFACTURING THE SAME

FIELD OF THE INVENTION

The present invention relates to a gas sensor using an n-type metal oxide semiconductor and a method of manufacturing such a gas sensor. More particularly, it relates to a gas sensor for detecting an inflammable gas and the method for manufacturing the same.

DESCRIPTION OF THE PRIOR ART

The sensitivity for a specific gas, S(gas), is determined from the following formula (1) and is defined as the ratio between the sensor resistance R(air) in dry air and the sensor resistance R(gas) when the gas to be detected is contained at a concentration of 3500 ppm, for example, in dry air.

$$S(gas) = R(air)/R(gas) \quad (1)$$

For instance, the sensitivity for methane $S(CH_4)$ is:

$$S(CH_4) = R(air)/R(CH_4)$$

wherein $R(CH_4)$ is the sensor resistance for methane $CH_4$.

As an index for the gas species selectivity, the sensitivity ratio T(gas 1/gas 2) is obtained from the following formula:

$$T(gas\ 1/gas\ 2) = S(gas\ 1)/S(gas\ 2) \quad (2)$$

wherein S(gas 1) is the sensitivity for a particular species of gas, and S(gas 2) is the sensitivity for another species of gas.

The sensitivity ratio of methane $CH_4$ and hydrogen gas $H_2$ is given by:

$$T(CH_4/H_2) = S(CH_4)/S(H_2)$$

while the sensitivity ratio for methane $CH_4$ and ethanol $C_2H_5OH$ is given by $$T(CH_4/C_2H_5OH) = S(CH_4)/S(C_2H_5OH).$$

The gas sensor for city gas, particularly city gas 13A which is comprised mainly of natural gas as defined by the Japanese Law Concerning Gas Business, is required to have equally high sensitivities for both methane and hydrogen gas, while the sensitivity for ethanol which is produced during cooking should be low. For instance, in gas sensors used in alarms for detecting city gas leaks, the sensitivity ratio for methane and hydrogen gas $T(CH_4/H_2)$ should be close to 1, while that for methane and ethanol $T(CH_4/C_2H_5OH)$ should be greater than 0.5. $T(CH_4/C_2H_5OH)$ should preferably be as large as possible.

Semiconductor gas sensors for detecting inflammable gases (hereinafter exemplified by methane) currently in extensive use are manufactured by sintering n-type metal oxide semiconductors. However, the sintering process is not satisfactory with respect to product reliability, stability and durability as it involves complex steps of manufacture and a number of factors which affect product performance. As it is difficult to reduce the size of the sintered products to below a certain limit, power consumption tends to increase. Development of thin film semiconductor gas sensors to take the place of such conventional sintered sensors is now under way, but no product has yet been developed which can replace the same.

One of the problems in the practical application of thin film semiconductor gas sensors is that such sensors can barely detect methane, although they are very effective in the detection of hydrogen. In order to circumvent this problem, various methods re proposed; such as forming an $SiO_2$ insulation film by oxidizing silicon substrate, and then forming Pt-doped $SnO_2$ film thereon (Japanese Laid-open Patent Application No. Sho 54-24094); and doping P or B on the silicon substrate on which the $SiO_2$ insulating layer has been formed (Japanese Laid open Patent Application No. Sho 54-24094). However, neither of these methods can achieve a uniform doping of dopant atoms and fail to attain the above-mentioned effects.

Another method is by forming by sputtering a super minute particle thin film of an n-type semiconductor mainly comprising metal oxides such as $SnO_2$, and then contacting the thin film with the electrodes. For example, Japanese Laid-open Patent Application No. Sho 59-83046 discloses a gas sensor provided with a sensor such that a super minute particle thin film of $SnO_2$, $ZnO$, $Cr_2O_3$, $Fe_2O_3$ or $TiO_2$ is contacted with electrodes. This thin film is an n-type compound semiconductor formed by sputtering, and has a low sensitivity for ethanol at the operating temperature of 450° C. and a high sensitivity for methane to change its resistivity.

The conventional type thin film semiconductor gas sensor cannot fully satisfy the condition of the sensitivity ratio of methane and hydrogen gas, $T(CH_4/H_2)$, and the sensitivity ratio of methane and ethanol, $T(CH_4/C_2H_5OH)$, and this tendency was more noticeable when the humidity in the atmosphere was high.

The present invention therefore overcomes the above-mentioned problems in the prior references and provides a gas sensor of which $T(CH_4/H_2)$ is close to 1, and $T(CH_4/C_2H_5OH)$ is greater than 0.5.

DETAILED DESCRIPTION OF THE INVENTION

According to an aspect of the present invention, there is provided a gas sensor of the type provided with n-type metal oxide semiconductor thin film which changes the resistivity according to the gas species detected which is characterized in that the thin film is provided with an insulating oxide film on its surface. Gases such as methane, hydrogen gas and ethanol with varying degrees of combustion, diffuse through the metal oxide film insulator and gases become partially combusted before they reach the n-type metal oxide semiconductor film, thereby adjusting the sensitivity ratio.

The n-type metal oxide semiconductor film preferably consists of $SnO_2$. In place of $SnO_2$, it may consist of $ZnO$, $Cr_2O_3$, $Fe_2O_3$ or $TiO_2$. These metal oxides are electrical insulators if they are in the state of complete oxidation, while an oxygen deficiency induces n-type semiconductor properties. When such metal oxides are used in a gas sensor, it is necessary to control the amount of gas if an optimal degree of conductivity was to be achieved. In practice, since an oxygen deficiency occurs at the time of film formation, oxygen is supplied by reaction sputtering or oxidation treatment is given after the film is formed to thereby control conductivity. N-type metal oxide semiconductors should preferably have a crystal structure with a large contacting area with gas. Super minute particle film may be used for such a crystal structure, but as disclosed by the present applicants in their Japanese Patent Application No. Sho 61-152585, it should preferably have a columnar crystal structure of 0.001 to 10 μm diameter in the direction substantially perpendicular to the substrate surface, and the mean distance at the non-fused part between adjacent columnar crystals being at least 30% of the length of columnar crystals.

The thickness of the oxide film insulator is preferred to be 0.005 to 3 μm in view of response characteristics, ethanol detection sensitivity, and so forth. The film should preferably contain one or more oxides selected from the group consisting of $SiO_2$, $MnO_2$, MnO and $V_2O_5$.

The crystal structure of an oxide film insulator should preferably have a regular columnar structure because of the required reaction with ethanol and passing methane and hydrogen gas therethrough.

According to another aspect of the present invention, there is provided a method for forming an oxide film insulator having a regular columnar crystal structure on the n-type metal oxide semiconductor thin film. This method of manufacturing gas sensors comprises a first step of forming an n-type semiconductor thin film of which resistivity changes as it senses gas on the substrate surface, a second step of forming film electrodes placed opposedly on the n-type semiconductor thin film, and a third step of providing a plate-like mask in contact with the electrodes and forming an oxide film insulator through the opening of the mask by sputtering on the surface of said n-type metal oxide semiconductor thin film. This method is characterized in that the opening of said mask extends from the side where the electrodes are opposing the electrode side for a distance of at least 1.5 times the thickness.

In this method, an n-type metal oxide semiconductor thin film should preferably have a columnar crystal structure, and therefore said film should preferably be formed by reaction sputtering in the first stage.

Although it is possible to form an oxide film insulator by vacuum evaporation of CVD, these methods have problems associated with them in that the crystal structure of the thin film is unstable, the yield of gas sensor manufacture is low, and that it is impossible to manufacture an oxide film insulator with a large bonding capacity. Even when sputtering is used in manufacturing the oxide film insulator, sputtering particles are reflected by the mask edge used for forming the film and enter the film. Thus, it is impossible to obtain a film with a regular columnar structure and to achieve the required sensitivity ratio as described above.

In the case of the present invention, sputtering particles for forming the oxide film insulator are reflected by the mask edges, and enter the film to form an irregular structure. In this invention, however, the edges which form the mask holes are opposed at positions distanced at least 1.5 times the thickness of the mask from the side edges where the electrodes are opposedly placed, therefore limiting the area with an irregular structure to the top surface of electrodes. An oxide film insulator having a regular columnar structure is formed on the n-type metal oxide semiconductor film which senses the gas. As the film is formed by sputtering, the bonding ability further improves. According to the present invention, there is provided a gas sensor which effectively detects hydrocarbon gas even in the presence of other gases such as ethanol, and such a gas sensor is most suitable for detection of city gas leaks.

According to the present invention, if the portion of the n-type metal oxide semiconductor film used for gas detection is formed as a narrow strip, the oxide film insulator formed thereon has a regular columnar structure and the narrow strip of n-type metal oxide semiconductor film functions effectively. This enables the manufacture of gas sensors with high sensitivity and selectivity for gases. The present invention, also, enables the production of small-sized gas sensors.

The embodiments of the present invention are now described by referring to the attached drawings.

EXAMPLES

Figure 1:
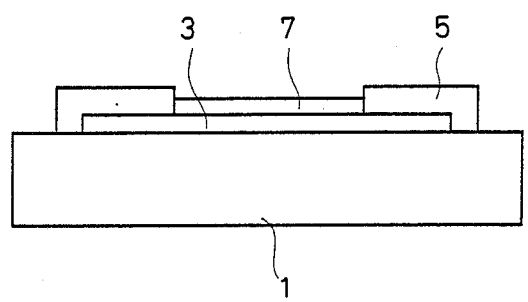
FIG. 1 is a cross-sectional view of the first and the second examples of the gas sensor of the present invention.

Referring to the first and the second example gas sensors shown in FIG. 1, an insulating substrate 1 is obtained by forming an $SiO_2$ insulator on silicon substrate or on a sapphire substrate according to a conventional method. An $SnO_2$ n-type metal oxide semiconductor film 3 is formed on the insulating substrate 1 by a PVD or CVD method. Electrodes 5 are made of, for example, platinum. The structure described above is substantially similar to that of well known inflammable gas sensors, and there are no limitations on the materials or methods of manufacture therefor. In the present examples, there are provided an oxide film insulator 7 of $SiO_2$, MnO, $V_2O_5$, and so forth, on the n-type metal oxide semiconductor film 3. The insulator 7 may comprise a single layer of a single oxide, or multiple layers of, for instance, $SiO_2$ and $MnO_2$ (regardless of the order of lamination). The insulator 7 should preferably have the thickness of 0.005 to 3 μm in view of the response characteristics or ethanol detection sensitivity. The insulator 7 may be formed by well known film forming methods such as a PVD or CVD method.

According to the gas sensor of the present invention, ethanol with a higher reactivity contained in the inflammable gas begins to react with the oxide on the surface of the insulator 7 and the concentration begins to decrease as it passes the film. When the inflammable gas reaches the n-type metal oxide semiconductor thin film 3, the sensitivity ratio $T(CH_4/C_2H_5OH)$ increases to facilitate the selective detection of $CH_4$.

The preferred embodiments and the comparative examples of the present invention are described below to further delineate the salient features of the present invention.

COMPARATIVE EXAMPLE 1

After forming an n-type $SnO_2$ thin film of 1 μm thickness on the sapphire substrate by reaction sputtering under the following conditions, a Pt electrode was formed by sputtering to obtain a gas sensor. The resistivity of an n-type $SnO_2$ thin film was 2 Ω cm in a 500° C. nitrogen atmosphere and 1000 Ω cm in an ambient atmosphere.

| Sputtering conditions | |
|---|---|
| Target | $SnO_2$ |
| $Ar/O_2$ ratio | 1.0 |
| Output | 150 W |
| Substrate temperature | 150° C. |

Figure 2:
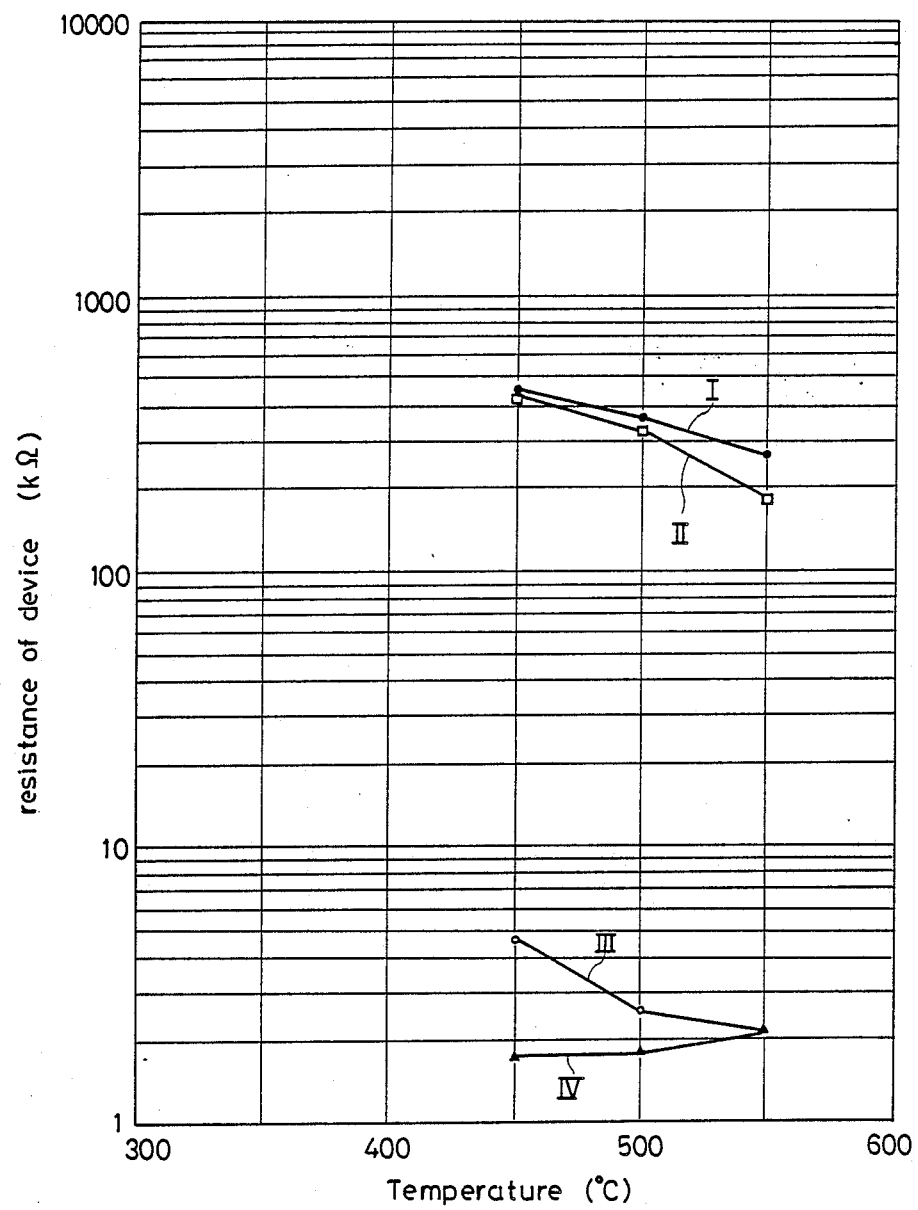
FIG. 2 is a graph showing the results of gas detection by Comparative Example 1.

Using the air samples containing methane at 3500 ppm, hydrogen 3500 ppm or methanol 2000 ppm, the gas sensor obtained was studied for its performance, and the results are shown in FIG. 2.

Figure 3:
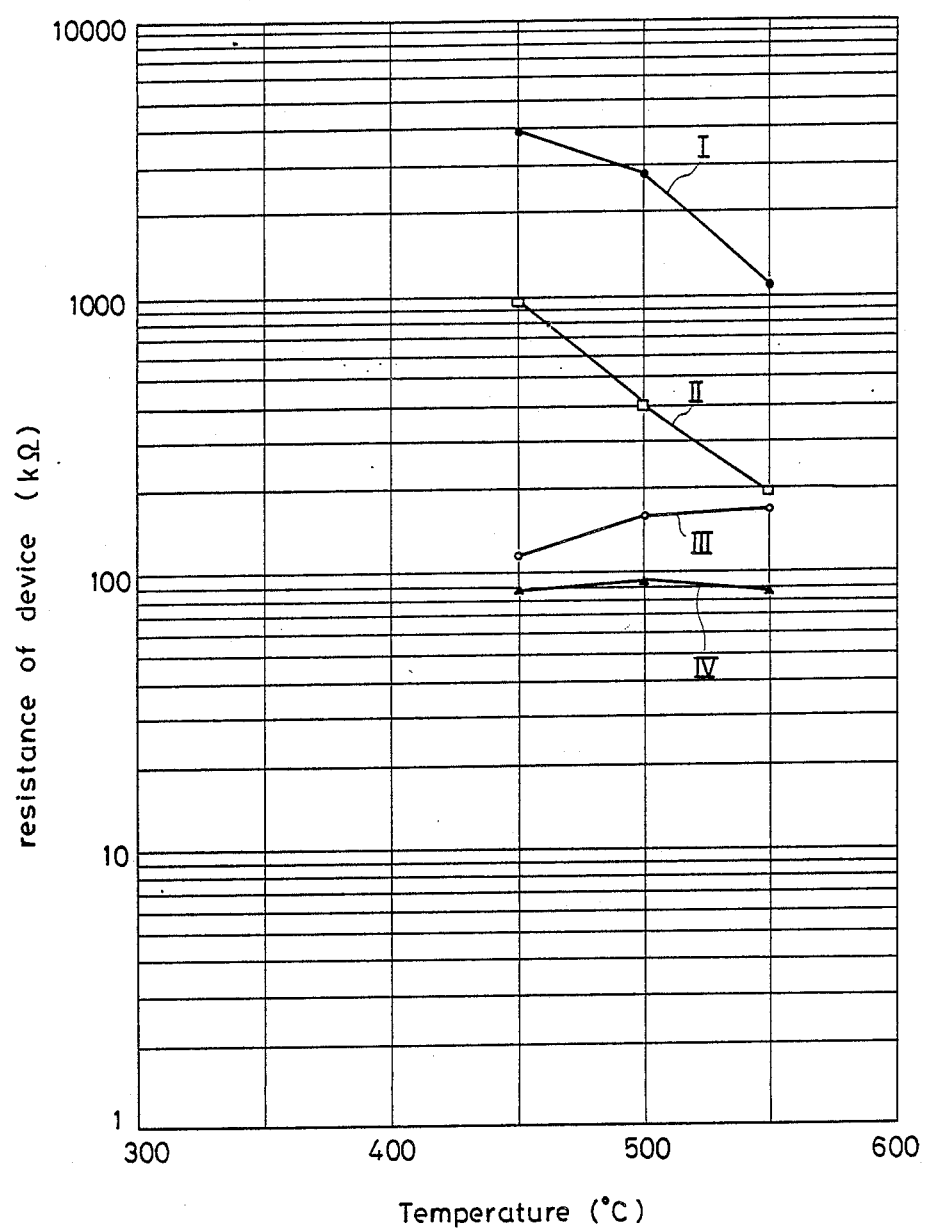
FIG. 3 is a graph showing the results of gas detection by the gas sensor according to the 1st Example of the present invention.

FIG. 2 as well as FIG. 3 shows the results of Example 1, and curves (I) to (IV) show the results of the following gases:

Curve (I): air
Curve (II): methane-containing air
Curve (III): ethanol-containing air
Curve (IV): hydrogen-containing air The sensitivity ratio expressed as $T(CH_4/C_2H_5OH)$ in this comparative example gas sensor was approximately 0.01 at 550° C.

EXAMPLE 1

An $SiO_2$ film of 0.3 μm thickness on an $SnO_2$ thin film of the gas sensor obtained in the Comparative Example 1 by the sputtering method. The gas detection performance for this sensor was studied using similar gases as in Comparative Example 1. The results are shown in FIG. 3. In the gas sensor of the present example, the sensitivity ratio expressed as $T(CH_4/C_2H_5OH)$ was approximately 0.5° or higher at 550° C., demonstrating that this sensor exhibited an excellent selectivity for $CH_4$.

EXAMPLE 2

A gas sensor was manufactured similarly to Example 1 except that the n-type $MnO_2$ film was formed in place of $SiO_2$ film. The gas sensor demonstrated that the hydrocarbon detection performance which was substantially similar to that of the gas sensor according to the Example 1.

EXAMPLE 3

The Examples 1 and 2 concerned cases where the oxide film is formed only on the n-type metal oxide semiconductor. Although these examples obtain detection performance of a certain degree, further improved performance is obtained by making the crystal structure of the oxide film into a regular columnar one. This is explained hereinbelow as the third example of this invention.

Figure 4:
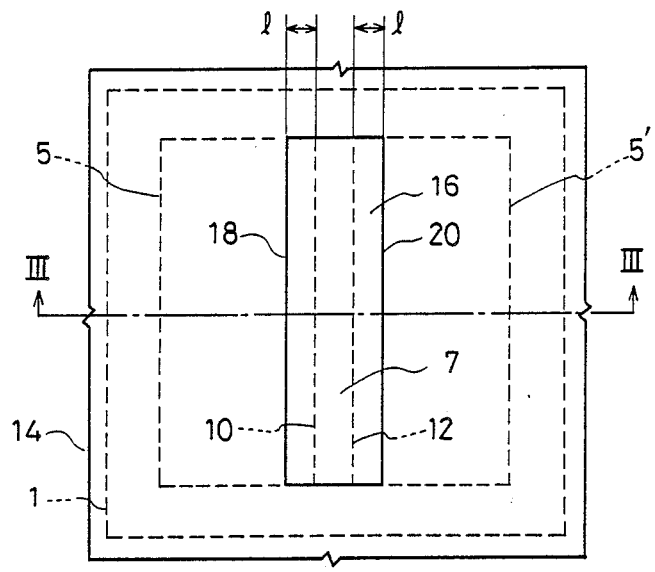
FIG. 4 is a plan view of the gas sensor according to the third Example of the present invention and the mask used in manufacture thereof.
Figure 5:
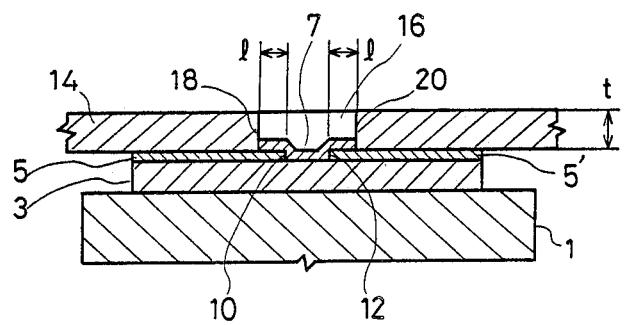
FIG. 5 is a cross-sectional view along the line V—V in FIG. 4.

FIG. 4 shows the plane view of the third example gas sensor with a mask, and FIG. 5 is a cross sectional view along the line V—V in FIG. 4. The vertical dimension in FIG. 5 is different from the actual dimensions in order to facilitate understanding.

The gas sensor according to the 3rd Example is manufactured as follows. An n-type metal oxide semiconductor film 3 made of $SnO_2$ having a size of, for instance, 1.8 mm×1.8 mm and thickness of 1 μm is formed on an insulating substrate 2 of sapphire, having an area of 2.3 mm,×2.3 mm by sputtering. The insulating substrate 1 is not limited to sapphire alone, and can be any insulating material so long as the n-type metal oxide semiconductor film 3 can be formed thereon. The semiconductor film 3 may be of ZnO or others instead of $SnO_2$ if the resistivity changes as it senses gases.

Two rectangular shaped film electrodes 5,5' are formed over the surface of the n-type metal oxide semiconductor film 3. The rectangular shaped film electrodes 5,5' are placed at opposite sides from one another and may be made of platinum having 0.3 μm thickness by sputtering using a mask so that the portion at the center having, for example, the width of 0.2 mm is excluded from sputtering. The two electrodes 5,5' then will have the dimensions of 1.8 mm×0.8 mm, and the distance between the two opposing sides 10,12 will be 0.2 mm, where the n-type metal oxide semiconductor film 2 is exposed. The electrodes 5,5' need not be made of platinum, but materials with high electric conductivity such as gold, silver or aluminum may be used.

After forming the electrodes 5,5', a plate-shaped mask 14 is positioned thereon. The mask is larger than the insulating substrate 1 in its outer periphery, has a thickness t of, for example, 0.02 mm, and an opening 16 at the center thereof. For the dimensions mentioned above, the opening should be approxmately 1.8 mm×0.5 mm. The mask 14 is so positioned that the portion of the n-type metal oxide semiconductor film 3 is not covered by the electrodes 5,5' and is fully exposed at the center of the opening 16. The electrodes 5,5' will both have the portion having the width 1 and opposing each other exposed. In the examples described previously, the length of the 1 is 0.15 mm. In other words, two edges 18,20 positioned parallel to the side edges 10,12 as if to transverse the electrodes 5,5', are positioned at points spaced by the distance 1=0.5 mm from the side edges 10,12, the magnification k being 7.5 times the thickness t of 0.02 mm of the mask 14. In k=1/t, k should be 1.5 or more an preferably more than 10.

On the uncovered portions of the n-type metal oxide semiconductor film 3 and the electrodes 5,5' an insulator 7 in a thickness of 3000 angstrom of, for example, $SiO_2$ is formed by sputtering. Sputtering particles for forming the insulator 7 are reflected by the edges 18,20 of the mask 14 to enter the film and form an irregular structure therein. The region where such an irregular structure is formed in the insulator 7 is limited to the area at a distance from the edges 18,20 by 1.5 times the thickness of the mask 14. In the present example, however, the edges 18,20 are positioned at a distance 7.5 times the thickness of the mask 14 from the side edges 10,12 where the electrodes 5,5' oppose each other, so that an oxide film insulator 7 having a regular columnar structure is formed on the n-type metal oxide semiconductor film 3 which senses the gas. As this film is formed by sputtering, its bonding force is large and its structure a regular columnar structure. The insulator 7 should preferably have the film thickness ranging between 0.01 and 1 μm, particularly between 0.1 and 0.5 μm.

Figure 6:
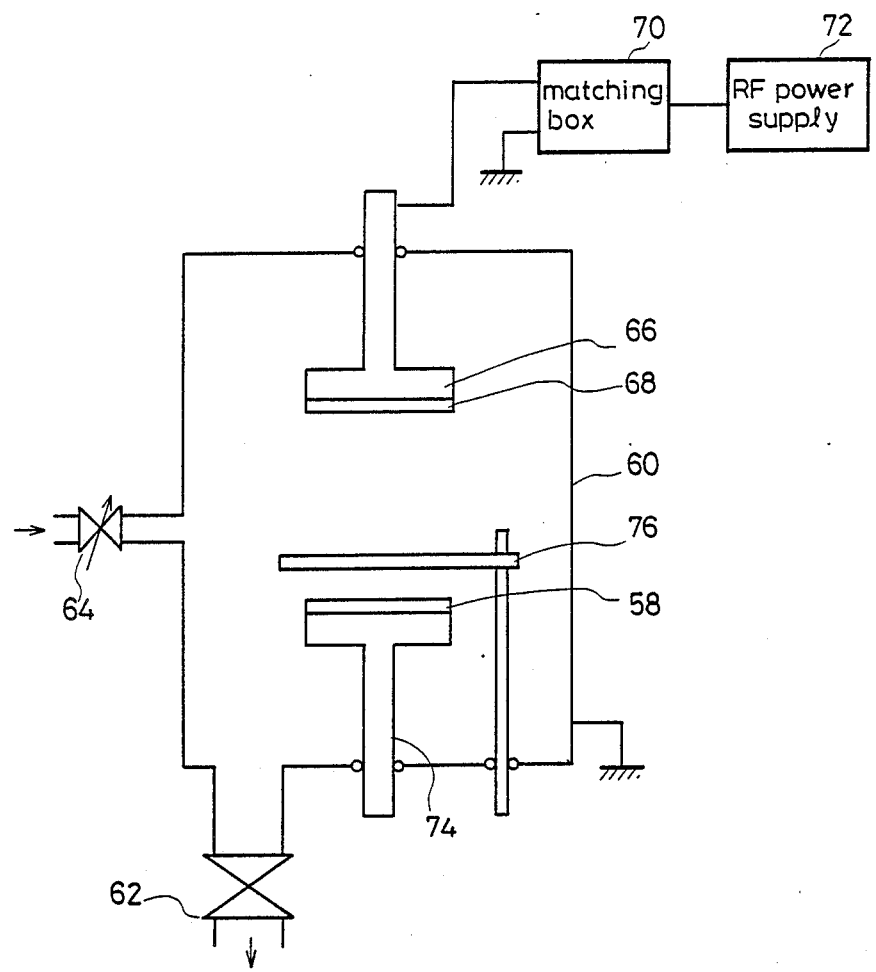
FIG. 6 is a schematic view of a sputtering device for forming an oxide film insulator used in the manufacture of the gas sensor.

FIG. 6 shows a schematic view of the sputtering device used for forming the insulator 7. The figure shows a case of RF sputtering, but the present invention is in no way limited to this method.

A vacuum chamber 60 is grounded and connected to a vacuum system consisting of a vacuum pump, etc. (not shown) at the lower side thereof by a main valve 62. Argon gas which is the carrier gas is chargeable at a constant rate from the side of the vacuum chamber 60 by a mass flow controller 64. An electrode 66 at the upper part of the vacuum chamber 60 and a target 68 attached beneath the electrode 66 are provided. When forming an oxide film insulator of $SiO_2$, a target 68 made of sintered $SiO_2$, is usually employed. The electrode 66 is led outside the vacuum chamber 60 and connected to an RF power source 72 by matching box 70. At the top of a substrate holder 74 is provided a member 58 with the mask 14 thereon as described above by the insulating substrate 1 formed with the n-type metal oxide semiconductor film 3 and the electrodes 5,5'. Between the target 68 and the member 58 is positioned a shutter 76 which may be rotated by manipulation outside the vacuum chamber.

When using the sputtering device previously described, the main valve 62 is first opened to provide a high vacuum at the inside of the vacuum chamber 60. The mass flow controller 64 is then controlled to introduce argon gas as a carrier gas at the constant flow rate of, for instance, 10 cc/min., and the pressure at the inside of the vacuum chamber 60 is set at, for example, $2.0 \times 10^{-2}$ Torr. The RF power source 72 is switched on with the shutter 76 closed, and an RF power of, for example 150W is then led to the electrode 66 in the chamber 60 to produce argon plasma at the front of the target 68. Insulating oxide particles are then sputtered outside the target impinged by argon ions. The target surface 68 is thus cleaned by pre-sputtering, and then the shutter 76 is opened, for instance, 10 minutes to deposit sputtering particles on the member 58. The insulator 7 made of $SiO_2$ was thus formed in a film thickness of 3000 angstrom. If oxidation of the insulator 7 is insufficient, oxygen gas is introduced along with the introduction of argon gas.

COMPARATIVE EXAMPLE 2

In order to confirm the effect of the mask 14, an n-type metal oxide semiconductor film 3 of $SnO_2$ and platinum electrodes 5,5' are formed on the sapphire insulating substrate 1 in a manner similar to the gas sensor in Example 3. An $SiO_2$ oxide film insulator 7 was formed on the gas sensor by sputtering, by replacing the mask alone. The insulator had the film thickness which was the same as that in Example 3. The film was also formed on an n-type metal oxide semiconductor 3 and platinum electrodes 5,5' by sputtering.

The mask used in the comparative example is 0.1 mm in thickness and the opening 1.8 mm×0.3 mm. The n-type metal oxide semiconductor film 3 is uncovered in a width of 0.2 mm which is the same as Example 3, but the width 1 of that is 0.05 mm for either of the electrodes 5,5'. In this case, the magnification k is 0.5 as obtained from k=1/t and is smaller than 1.5.

Table 1 shows the results of the measurements of the two gas sensors of the Example 3 and the Comparative Example 2 at the operating temperatures of 450° C. and 500° C.; the measured values were:
sensitivity for methane $CH_4$: $S(CH_4)$
sensitivity for hydrogen gas $H_2$: $S(H_2)$, and
sensitivity for ethanol $C_2H_5O$: $S(C_2H_5OH)$ The concentration of these gases was 3500 ppm. Based on these measured values, the following ratios were computed and shown in Table 2.
Sensitivity ratio of methane and hydrogen
... $T(CH_4/H_2)$
Sensitivity ratio of methane and ethanol
... $T(CH_4/C_2H_5OH)$ Table 2 discloses that $T(CH_4/H_2)$ is improved to almost 1 in the gas sensor of Example 3. $T(CH_4/-C_2H_5OH)$ is also radically improved to reach the value much larger than 0.5.

In the above description, the n-type metal oxide semiconductor film 3 and the electrodes 5,5' were manufactured by the sputtering method, but they may be made by vacuum evaporation, CVD or PVD other than sputtering. The shape of electrodes 5,5' is not limited to a rectangle, but it may be any shape so long as they are opposing electrodes having opposing side edges. The insulating substrate 1 may be a large substrate instead of a small sized one as in the above, and a plurality of gas sensors may be formed concurrently on such a substrate and then cut into individual sensors.

TABLE 1

| Sensitivity | Temperature °C. | According to the comparative experiment k = 0.5 | According to the present invention k = 7.5 |
|---|---|---|---|
| $S(CH_4)$ | 450 | 8.1 | 15.2 |
| | 500 | 4.2 | 9.2 |
| $S(H_2)$ | 450 | 39.6 | 24.6 |
| | 500 | 49.3 | 8.6 |
| $S(C_2H_5OH)$ | 450 | 18.7 | 7.2 |
| | 500 | 9.1 | 2.0 |

TABLE 2

| Sensitivity ratio | Temperature °C. | According to the comparative example k = 0.5 | According to the present invention k = 7.5 |
|---|---|---|---|
| $T(CH_4/H_2)$ | 450 | 0.20 | 0.62 |
| | 500 | 0.09 | 1.07 |
| $T(CH_4/C_2H_5OH)$ | 450 | 0.43 | 2.11 |
| | 500 | 0.46 | 4.6 |

What is claimed is:

1. A gas sensor comprising a thin film of an n-type metal oxide conductor which changes resistivity according to the gas species detected, and an insulting film on a surface of said thin film, wherein the oxide film insulator contains one or more oxides selected from the group consisting of $SiO_2$, $MnO_2$, MNO and $V_2O_5$.

2. A gas sensor as in claim 1, wherein the metal oxide semiconductor film comprises $SnO_2$.

3. A gas sensor as in claim 1, wherein the n-type metal oxide semiconductor film has a columnar crystal structure.

4. A gas sensor as in claim 1, wherein the oxide film insulator is 0.005 to 3 μm in thickness 5. A gas sensor as in claim 4, wherein the oxide film insulator is 0.01 to 1 μm in thickness.

6. A gas sensor as in claim 4 wherein the oxide film insulator is 0.1 to 0.5 μm is thickness.

7. A gas sensor as in claim 1 wherein the oxide film insulator has the columnar crystal structure.

* * * * *